United States Patent
Deck et al.

(10) Patent No.: US 11,433,182 B2
(45) Date of Patent: Sep. 6, 2022

(54) DRUG DELIVERY DEVICE AND TRANSFER STATION

(71) Applicant: Roche Diabetes Care, Inc., Indianapolis, IN (US)

(72) Inventors: Frank Deck, Mannheim (DE); Hans List, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 172 days.

(21) Appl. No.: 16/422,840

(22) Filed: May 24, 2019

(65) Prior Publication Data

US 2019/0275243 A1 Sep. 12, 2019

Related U.S. Application Data

(63) Continuation of application No. PCT/EP2017/081588, filed on Dec. 5, 2017.

(30) Foreign Application Priority Data

Dec. 6, 2016 (EP) ..................... 16202355

(51) Int. Cl.
*A61M 5/168* (2006.01)
*A61J 1/20* (2006.01)
(Continued)

(52) U.S. Cl.
CPC ............ *A61M 5/16827* (2013.01); *A61J 1/20* (2013.01); *A61J 1/2003* (2015.05); *A61J 1/22* (2013.01);
(Continued)

(58) Field of Classification Search
CPC ............ A61M 5/14248; A61M 5/1723; A61M 5/172; A61M 5/14276; A61M 5/14244;
(Continued)

(56) References Cited

U.S. PATENT DOCUMENTS

| 5,814,015 A | * | 9/1998 | Gargano | ............. A61M 5/1456 604/67 |
| 2004/0082937 A1 | * | 4/2004 | Ausiello | ................ A61K 38/29 604/891.1 |

(Continued)

FOREIGN PATENT DOCUMENTS

| CA | 2 904 121 A1 | 9/2014 |
| EP | 2 866 163 A2 | 4/2015 |

(Continued)

OTHER PUBLICATIONS

International Seach Report and Written Opinion of the International Searching Authority, PCT/EP2017/081588, dated Feb. 20, 2018, 17 pages.

*Primary Examiner* — Manuel A Mendez
(74) *Attorney, Agent, or Firm* — Bose McKinney & Evans LLP

(57) ABSTRACT

A drug delivery device comprises first and second liquid drug reservoirs and first and second outlet ports. A drive is configured for expelling a first liquid drug from the first reservoir to the first outlet port and for expelling a second liquid drug from the second reservoir to the second outlet port. A memory is provided that contains a drug dosing scheme specifying a desired liquid drug type, and at least one sensor is provided that detects information concerning the type of liquid drug contained in the first and/or second reservoir. A processor receives the information from the at least one sensor and thereby determines the type of liquid drug retained in the first reservoir and/or the second reservoir, and uses the drug dosing scheme and the determined type of liquid drug to operate the drive. Associated devices this disclosure and methods are also disclosed.

19 Claims, 5 Drawing Sheets

(51) Int. Cl.
    *A61M 5/14*          (2006.01)
    *A61M 5/142*       (2006.01)
    *A61J 1/22*          (2006.01)
    *A61M 5/36*         (2006.01)
    *G16H 20/17*       (2018.01)

(52) U.S. Cl.
    CPC ...... *A61M 5/1408* (2013.01); *A61M 5/14248* (2013.01); *A61J 2205/00* (2013.01); *A61J 2205/60* (2013.01); *A61M 5/365* (2013.01); *A61M 2005/14208* (2013.01); *A61M 2205/18* (2013.01); *A61M 2205/3306* (2013.01); *A61M 2205/3324* (2013.01); *A61M 2205/3368* (2013.01); *A61M 2205/3379* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/584* (2013.01); *A61M 2205/587* (2013.01); *A61M 2205/6054* (2013.01); *A61M 2205/6063* (2013.01); *A61M 2209/045* (2013.01); *G16H 20/17* (2018.01)

(58) Field of Classification Search
    CPC .......... A61M 5/142; A61M 5/24; A61M 5/20; A61M 5/31568; A61M 5/5086; A61M 5/1452; G16H 20/17; G16H 20/13
    See application file for complete search history.

(56) References Cited

U.S. PATENT DOCUMENTS

| | | | |
|---|---|---|---|
| 2005/0277912 A1* | 12/2005 | John | G16H 20/17 604/890.1 |
| 2011/0009817 A1* | 1/2011 | Bennett | G01N 21/17 604/93.01 |
| 2013/0079708 A1* | 3/2013 | Wimpenny | A61M 5/19 604/65 |
| 2013/0178791 A1* | 7/2013 | Javitt | A61M 5/14248 604/66 |

FOREIGN PATENT DOCUMENTS

| | | |
|---|---|---|
| WO | WO 2012/110474 A1 | 8/2012 |
| WO | WO 2014/029433 A1 | 2/2014 |

\* cited by examiner

DRUG DELIVERY DEVICE AND TRANSFER STATION

RELATED APPLICATIONS

This application is a continuation of PCT/EP2017/081588, filed Dec. 5, 2017, which claims priority to EP 16 202 355.0, filed Dec. 6, 2016, the entire disclosures of both of which are hereby incorporated herein by reference.

BACKGROUND

This disclosure relates to a drug delivery device and a transfer station.

Drug delivery devices are medical devices that provide prescribed fluids to patients. For example, medication such as antibiotics, chemotherapy drugs and insulin are commonly delivered to patients via a drug delivery device. For example, WO 2014/029433 A1 discloses a transfer station for transferring a medical fluid between a supply container and an administration container of an infusion device comprising at least one port for fluidic connection of a supply container to the transfer station and a further port for fluidic connection of the administration container to the transfer station. A transfer mechanism for automatically transferring a predetermined amount of medical fluid from the at least one supply container to the administration container, and an electronic processing unit connected to an actuation means are provided.

SUMMARY

This disclosure teaches an improved transfer station, an improved method for operating a transfer station, a drug delivery device, a method of operating a drug delivery device, a system comprising a transfer station and a drug delivery device, a method for operating such a system and computer program product.

Embodiments relate to a drug delivery device for a user, the device comprising a first reservoir for retaining a first liquid drug, a second reservoir for retaining a second liquid drug, a first outlet port and a second outlet port, a drive for expelling the first liquid drug from the first reservoir and for expelling the second liquid drug to the first outlet port and from the second reservoir to the second outlet port, the device further comprising a processor and a memory, the memory comprising a drug dosing scheme and instructions, the drug dosing scheme specifying a desired liquid drug type, wherein executing of the instructions by the processor causes the processor to control the drug delivery device to
  determine the type of liquid drug retained in any of the first reservoir and the second reservoir,
  in accordance with the drug dosing scheme and the determined type of liquid drug, operate the drive.

Embodiments of this disclosure may have the advantage that the drug delivery device may be operated in a safe manner even though two reservoirs are provided at the same time for the drug delivery device.

For example, the first liquid drug may be insulin, whereas the second drug may be glucagon. The human body requires that the blood glucose level is maintained in a very narrow range. Homeostasis is regulated by two hormones, insulin and glucagon which are both secreted by the endocrine pancreas. In response to insulin, cells absorb glucose out of the blood, having the net effect of lowering the high blood glucose levels into the normal range. On the contrary, the effect of glucagon is to make the liver release the glucose it has stored in its cells into the bloodstream, with the net effect of increasing blood glucose.

Thus, a drug delivery device having two reservoirs containing insulin and glucagon may therefore help a user to regulate both low and high blood sugar levels in a desired manner. Since, for example, in the situation of the high blood sugar level the exposure of the user to glucagon would further increase this already high blood sugar level which may result in a life-threatening situation for the user, the device as described above may have the benefit that an accidental administration of the wrong drug is prevented.

Generally, the drug dosing scheme may specify, besides the desired liquid drug type, the time and dosage for administration of the drug. Thus, the operation of the drive also may consider these criteria of the drug dosing scheme.

Further, generally the term "drive" has to be understood as a component that pushes the first or the second liquid drug from the respective reservoir through a dedicated respective flow path to a respective outlet port. Pushing of the liquid may for example be realized using a piston of the drive being adapted upon a linear movement of the piston within the respective reservoir to push the liquid drug towards the respective outlet port. The drive may comprise for example a single piston which depending on the desired drug moves towards the respective reservoir for subsequent pushing of the liquid drug. In another example, the drive may comprise a dedicated piston for each reservoir. A single motor of the drive may be used to perform the linear movement of the respective piston using a respective gear to selectively operate one of the pistons. Alternatively, the drive may have two motors, one motor assigned to the piston of the first reservoir and the other motor assigned to the piston of the second reservoir. Having only a single motor may have the advantage of cost savings.

In accordance with an embodiment of this disclosure, the operation of the drive is performed in order to deliver the liquid drug which type corresponds to the desired liquid drug type from its respectively determined first reservoir or second reservoir to the respective first or second outlet port. Thus, in this specific embodiment the first and the second reservoir may comprise different drugs in any variable order. Nevertheless, the device is able to ensure that the correct drug is administered to the user.

In accordance with an embodiment, the drug dosing scheme further specifies that the first reservoir has to contain the desired liquid drug type, wherein in case the type of the first liquid drug does not correspond to the desired liquid drug type, executing of the instructions by the processor further causes the processor to control the drug delivery device to provide a warning signal to the user via a user interface of the drug delivery device, the operation of the drive being performed such that delivery of any liquid drug from the first reservoir to the first outlet port is prevented. Thus, in this embodiment the device expects that the first liquid drug is of a specific type, for example, insulin or glucagon, and in case that specific type of drug is not available as the first liquid drug in the first reservoir, the device ensures that the user is informed accordingly regarding this problem and that this incorrect liquid drug is not administered to the user.

In accordance with an embodiment of this disclosure, the drug dosing scheme further specifies that the first reservoir or the second reservoir has to contain the desired liquid drug type, wherein in case neither the type of the first liquid drug nor the type of the second liquid drug corresponds to the desired liquid drug type, executing of the instructions by the processor further causes the processor to control the drug delivery device to provide a warning signal to the user via a user interface of the drug delivery device, the operation of the drive being performed such that delivery of any liquid drug to the outlet ports is prevented.

This may have the advantage of more a flexible way of using the two reservoirs. Either of these two reservoirs may contain the liquid drug with its desired type. However, in case neither of the reservoirs contains the desired liquid drug, it is ensured that the user is informed accordingly via the user interface and that an inappropriate drug is not accidentally administered to the user.

It has to be noted that throughout the description, a user interface of the device is understood as any kind of interface that is able to provide information to the user. This may include visible or audible or tactile information. Visible information may be provided by a graphical user interface which in basic configuration may only comprise one or more LEDs of one or more colors up to a graphical user interface like an LCD display with high-resolution. In the simple case the warning signal may just be the flash of a certain LED in a certain color or with a certain flashing rhythm, or in case of the high resolution graphical user interface it may be a text message that provides the warning to the user. Audible information may be a single tone at a given frequency or it may comprise a spoken text message. Tactile or sensible information may include a certain vibration of the device that indicates the warning to the user.

In accordance with an embodiment of this disclosure, the first liquid drug and the second liquid drug are identical. This may have the advantage that due to the enhanced availability of the liquid drug the user can use the drug delivery device for a longer time. For example, if under normal operation circumstances the first reservoir supports the user with liquid drug for the duration of two days, additional usage of the second reservoir which contains the same liquid drug extends the total usage of the device up to four days.

For example, the memory further comprises a threshold criterion, the execution of the instructions by the processor further causing the processor to control the drug delivery device to operate the drive to deliver the liquid drug from the first reservoir to the first outlet port,
    determining the amount of the drug in the first reservoir that is currently available to the user,
    compare the determined amount with the threshold criterion,
    in response to the comparison, in case the determined amount is lower than or equal to the threshold criterion, operate the drive to deliver the liquid drug from the second reservoir to the second outlet port, the threshold criterion specifying a residual availability of the drug provided in the first reservoir.

Thus, the device automatically monitors the amount of drug that is currently available to the user. In case a predefined threshold criterion is reached, the device may automatically switch the supply of the drug from the first reservoir to the second reservoir.

The amount of the drug that is currently available to the user may be the amount of the drug that is currently available in the first reservoir, the residual availability of the drug in the reservoir and the amount of the drug that is currently available in the reservoir being specified using any measurement unit of a remaining time period of use until the drug is used up,
    a remaining amount of individual boluses until the drug is used up,
    a remaining absolute amount of the drug,
    a remaining relative amount of the drug in relation to an amount of the drug that is maximally available in the reservoir.

All this may be determined based on the dosing scheme stored in the memory. For example, the dosing scheme specifies that a certain bolus has to be administered in certain time intervals, the device can easily calculate the remaining period of use or number of usages until the drug is used up.

In accordance with an embodiment of this disclosure, the first reservoir and the second reservoir have an assigned identifier, the identifier specifying the type of liquid drug retained in any of the first reservoir and the second reservoir, the determination of the type of the liquid drug retained in any of the first reservoir and the second reservoir comprising reading the identifier by the drug delivery device and determining from the read identifier the type of the liquid drug retained in any of the first reservoir and the second reservoir.

For that purpose, in the simplest case one tag is assigned to the two reservoirs together, which may for example specify the same type of liquid drug that is retained in both reservoirs. In another case, each reservoir may have assigned such a tag.

In accordance with an embodiment, the identifier is any of a optically readable tag,
    near field communication tag,
    magnetically readable tag,
    chip electronically readable,
    mechanically readable tag.

Here, each reservoir may have its own tag or both reservoirs may carry the common tag together which carries both identifiers for both reservoirs. Here, the identifiers may be different from each other regarding its content.

It has to be noted that an optically readable tag may be understood as a barcode, QR code or an alphanumeric code. Further, an optically readable tag may comprise a certain recess at a dedicated position relative to the first or second reservoir, wherein the spatial position of the recess is detectable via a light beam of the device. The spatial position of the recess hereby indicates the type of liquid drug that is contained in the respective reservoir.

A near field communication tag is understood as any tag which can be read out for example by RFID techniques.

And electronically readable chip may comprise a memory which can be electronically read out by the device. For that purpose, electrodes of the device may get in electrical contact with the chip. It is further possible, that the chip wirelessly communicates with the device.

A mechanically readable tag may comprise a certain recess or protrusion at a dedicated position relative to the first or second reservoir, wherein the spatial position of the recess is detectable via a mechanical finger of the device. Again, the spatial position of the recess hereby indicates the type of liquid drug that is contained in the respective reservoir.

In accordance with an embodiment of this disclosure, the determination of the type of the liquid drug retained in any of the first reservoir and the second reservoir comprises analyzing by the drug delivery device the first liquid drug and the second liquid drug. This may have the advantage that the risk of a wrong administration of a drug to a user is minimized since the decision of which reservoir to use for drug administration (or if the correct drug is available at all) is not based on information provided with the reservoir(s) but on information that is directly determined by the content of the reservoir and is detected by the device itself. Any information assigned to the reservoirs may become corrupted for various reasons. For example, in case of some types of tags a tag may be accidently modified or even actively manipulated even without knowledge of the user.

For example, the analyzing comprises any of an analysis of the
chemical properties,
physical properties.

Analysis of the chemical properties may comprise analysis of the pH-value of the drug or the chemical reactivity of the drug. The chemical reactivity may refer for example to a chemical reaction of the drug when interacting with another substance. The chemical reactivity of the drug may be used in order to determine in a specific manner one or more drug classes of the drug. Therefore, the respective reagent is required.

Analysis of the physical properties may comprise any of optical properties, fluidic density, electrical properties, thermal properties, solubility, viscosity of the drug. Optical properties may comprise any of a color, transparency, haze and absorption spectrum, refraction index of the drug. Electrical properties may comprise any of an electrical conductivity, impedance. Thermal properties may comprise any of the thermal conductivity, boiling point.

The optical properties of the drug may be determined through the transparent wall of either the respective reservoir retaining the drug or a transparent fluid path which connects the respective reservoir with the respective outlet port. A light source may be provided using an LED or a semiconductor Laser. Detection may be performed using a photosensitive semiconductor detector, e.g., in combination with color filters, diffraction gratings etc. Both, light source and detector, as well as filters are provided by the device.

For measurement of the electric conductivity or the pH value, electrodes may be necessary which get in contact with the liquid. For this purpose, either the fluid path between the respective reservoir and the respective outlet port is provided with a respective set of electrodes or a respective measurement cell such that pushing the part of the liquid currently contained in the respective reservoir by the drive towards the respective outlet port permits for analyzing this part of the liquid.

Measurement of the thermal properties of the liquid like for example the heat conductivity or heat capacity may be performed using a heating resistor. The heating resistor may be applied with the certain electric current over a certain time range and the resulting gradient of temperature within the liquid is measured over time.

Generally, for measurement of the properties of the liquid either respective measurement sensors or analyzers are provided for performing a measurement in the fluid path or in a small measurement cell attached to the fluid path, wherein the fluid path describes the path of the fluid between the reservoir and the respective outlet port. The measurement of the properties of the liquid drug in the fluid path may be beneficial since this could be performed in combination with a determination of the presence of air bubbles in the fluid path. The determination of the presence of air bubbles in the fluid path may in turn be beneficial since air bubbles may negatively influence the administration of the drug to the user. First of all, air bubbles in the bloodstream of the user are to be avoided in a general manner and second, air bubbles in the liquid drug lead to the corruption of the concentration of the active substance of the liquid drug such that the user may get administered a wrong dosage of the active substance. Thus, a common sensor or measurement cell may be used for both, determining the presence of air bubbles in the fluid path and determining the type of liquid drug.

The term 'analyzer' refers to a device being operable to execute one or multiple analyses on biological samples. An analyzer is operable to determine via various chemical, biological, physical, optical or other technical procedures a parameter of the sample or a component thereof, the parameter in the following being referred to as 'measurement value'. An analyzer is operable to measure said parameter of the sample or of at least one analyte and return the obtained measurement value. The list of possible analysis results returned by the analyzer comprises, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various type.

In another aspect, this disclosure relates to a device comprising a first reservoir for retaining a first liquid drug, a second reservoir for retaining a second liquid drug, a first outlet port and a second outlet port, a drive for expelling the first liquid drug from the first reservoir and for expelling the second liquid drug to the first outlet port and from the second reservoir to the second outlet port, the device further comprising a memory, the memory comprising a drug dosing scheme, the drug dosing scheme specifying a desired liquid drug type, the method comprising
  determining the type of liquid drug retained in any of the first reservoir and the second reservoir,
  in accordance with the drug dosing scheme and the determined type of liquid drug, operating the drive.

In another aspect, this disclosure relates to a transfer station for transferring a liquid drug between a supply container and a reservoir of a drug delivery device, the transfer station comprising a processor and a memory, the memory comprising instructions, wherein executing of the instructions by the processor causes the processor to control the transfer station to
  determine the type of liquid drug retained in the supply container,
  optionally transfer the liquid drug from the supply container to the reservoir,
  provide an identifier to the reservoir, the identifier specifying the type of liquid drug retained in the supply container.

The provision of the identifier to the reservoir can be either performed before, during or after the transfer of the liquid drug from the supply container to the reservoir. Either the transfer station can transfer the liquid drug from the supply container to the reservoir, or the user may do it manually.

It has to be noted that "the identifier specifying the type of liquid drug retained in the supply container" has to be understood without reference to time. In case for example the type of drug is determined after completion of the transfer of the drug from the supply container to the reservoir, the supply container may even be empty. Thus, the respective determination may be made using an analysis of the content of the reservoir, but the liquid in the reservoir is still the liquid that is (was) retained in the supply container.

In accordance with an embodiment of this disclosure, the provision of the identifier is comprising any of a
  printing of the identifier onto the reservoir, storing the identifier in a near field communication tag assigned to the reservoir, e.g., located on the reservoir storing the identifier in a magnetic tag assigned to the reservoir, electronic storing of the identifier in a chip assigned to the reservoir, mechanical modification of a predefined area of the reservoir.

In turn, a respective drug delivery device will be able to read the identifier, as described above in optical manner, mechanical manner etc.

In accordance with an embodiment of this disclosure, the transfer station is adapted to distinguish at least between two different ones of the type of liquid drug.

In accordance with an embodiment of this disclosure, the determination of the type of the liquid drug retained in the supply container comprises analyzing by the transfer station the liquid drug or reading an identifier of the supply container describing the type of the liquid drug.

In case the supply container already clearly identifies the liquid drug that is retained and provided by the supply container, it may be sufficient to trust this information.

It has to be noted here that the information that is provided by the supply container may in addition to the type of drug also indicate the shelf life of this drug, the dilution factor of this drug and other specific properties of the drug. This additional information may also be added to the identifier of the reservoir. This may enable the drug delivery device to accordingly adapt the administration of the drug such that it is ensured that the correct drug dosage is provided to the user.

The supply container may have all the information encoded or described in the same manner, as it was discussed above with respect to the reservoir or the supply container (optically readable printing, storing in an NFC tag or a magnetic tag etc.).

In accordance with an embodiment, the analyzing comprises any of an analysis of the chemical properties,
physical properties.

The chemical and physical properties may be the same as described above with respect to the drug delivery device. The respective measurements may be performed in an analogous manner. For the measurement of for example the physical properties, respective electrodes or sensors may either be provided again with a measurement cell attached to the fluid path or within the fluid path itself that interconnects the supply container with the reservoir.

In one embodiment, each new reservoir may comprise its own measurement cell. During filling of the reservoir using the supply container the drug may at least partially flow through the measurement cell or into the measurement cell. Thereupon, the measurement cell is able to perform the respective determination of the drug type by performing a respective measurement. After termination of the filling procedure and withdrawal of the reservoir, said measurement cell may automatically be separated from the reservoir and then disposed by the user. This may have the advantage, that a risk of corruption of measurements performed by the measurement cell is minimized. The risk of corruption may be higher the more different drugs the same measurement cell had already analyzed in the past. This may be due to for example remainders of drug particles that were remaining in the measurement cell from the previous the termination of the respective drug type.

The chemical properties of the drug may be determined with a respective reagent. For that purpose, the measurement cell may comprise a reagent for example given by a certain test strip. A user may enter the test strip into the measurement cell. The wetting of the reagent (e.g., using the test strip) may be performed using a capillary gap or a wick, which results in a certain reaction of the drug and the reagent. Capturing of the reaction may be performed, e.g., optically or electrochemically. An optical capturing of the reaction may typically be performed for example when the test strip is used for determining the pH value of the drug. The resulting coloring of the test strip corresponds to a certain pH value.

Instead of the above described withdrawal of the whole measurement cell, it may also be possible to just dispose (e.g., automatically) the test strip while the measurement cell either remains with the transfer station or with the reservoir. Thus, the measurement cell can be used multiple times for determining the drug type.

In another aspect, this disclosure relates to a method for operating a transfer station for transferring a liquid drug between a supply container and a reservoir of a drug delivery device, the method comprising determining by the transfer station the type of liquid drug contained in the supply container, optionally transferring automatically or manually the liquid drug from the supply container to the reservoir, providing by the transfer station an identifier to the reservoir, the identifier specifying the type of liquid drug contained in the supply container.

In another aspect, this disclosure relates to a system comprising a drug delivery device as described above and a transfer station as described above.

In another aspect, this disclosure relates to a method for operating a system comprising a drug delivery device and a transfer station, the device comprising first reservoir for retaining a first liquid drug, a second reservoir for retaining a second liquid drug, a first and a second outlet port, a drive for expelling the first liquid drug from the first reservoir and for expelling the second liquid drug to the first outlet port and from the second reservoir to the second outlet port, the device further comprising a memory, the memory comprising a drug dosing scheme, the drug dosing scheme specifying a desired liquid drug type, the method comprising determining by the transfer station the type of liquid drug contained in a supply container, transferring the liquid drug from the supply container to the first reservoir, providing by the transfer station an identifier to the reservoir, the identifier specifying the type of liquid drug contained in the supply container, by the drug delivery device determining the type of liquid drug retained in any of the first reservoir and the second reservoir, in accordance with the drug dosing scheme and the determined type of liquid drug, by the drug delivery device operating the drive.

In another aspect, this disclosure relates to a computer program product comprising computer executable instructions to perform the methods as described above.

It is understood that one or more of the aforementioned embodiments of this disclosure may be combined as long as the combined embodiments are not mutually exclusive.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
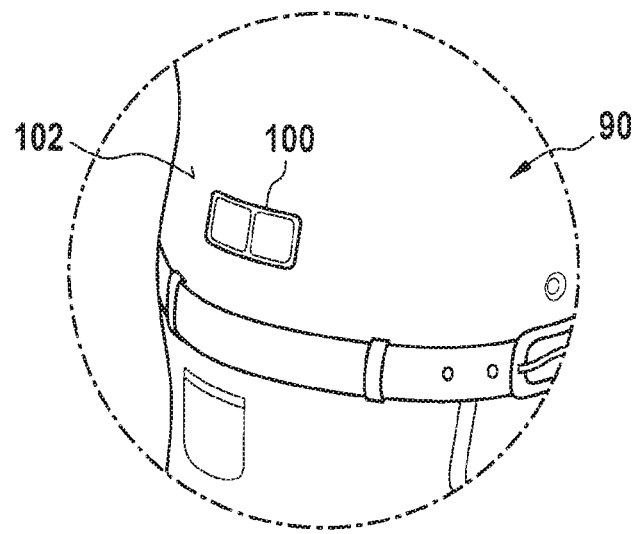
FIG. 1 is a schematic diagram of the portable liquid drug delivery device carried by a user.

FIG. 1 illustrates a schematic diagram of a portable liquid drug delivery device 100 that is currently carried by a user 90. The portable liquid drug delivery device 100 is adhered to the skin 102 of the user or patient 90. The drug delivery device 100 comprises a reservoir containing a certain drug like insulin which is injected by the device 100 through the skin 102 of the user in an automated manner using a drug dosing scheme electronically stored in the device 100.

Figure 2:
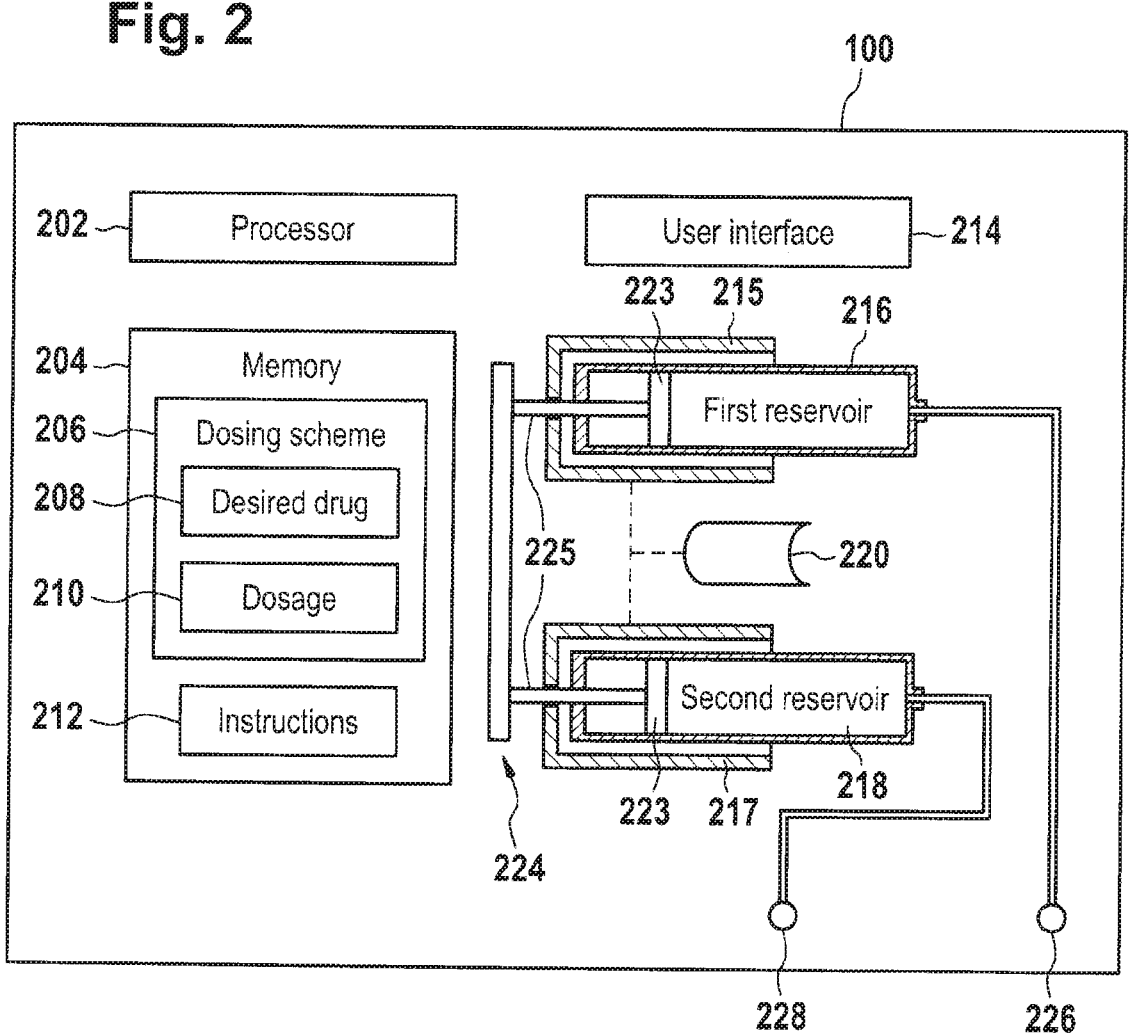
FIG. 2 is a schematic block diagram of the portable liquid drug delivery device.

FIG. 2 shows a more detailed block diagram of the drug delivery device 100. The device 100 comprises a processor 202 and a memory 204, wherein the memory 204 comprises the above-mentioned drug dosing scheme 206. The drug dosing scheme 206 specifies a certain type of desired drug 208 and a dosage 210. For example, the drug dosing scheme specifies that in certain time intervals the drug of type "insulin" is to be administered to the user 90.

Further, the memory 204 comprises instructions 212 relating to the operation of the device 100. Carrying out of the instructions enables the device to operate according to for example the flow diagrams of FIGS. 4, 5 and 6, as will be discussed below.

The drug delivery device 100 comprises as the reservoir a first reservoir 216 and the second reservoir 218 simultaneously. The reservoirs are received in the device via sockets 215 and 217, respectively. The first and second reservoirs have fluid paths that connect the two reservoirs with a first outlet port 226 and a second outlet port 228, respectively. Further, a drive 224 is provided that is adapted to move plungers 223 in the first and second reservoir via respective pistons 225. The purpose of the drive is to push the liquid drug contained in the first or second reservoir out of the respective reservoir over the respective fluid paths to the to the outlet port 226 and 228, respectively.

Not shown in the FIG. 2 is a unit well known from the prior art which may comprise for example an infusion set comprising a cannula cartridge unit which on top may have a self-sealing septum through which a penetrating member may be inserted. Said penetrating member may include a sharp tip and may be configured to penetrate the skin 102 of the patient or user to allow insertion and placement of the cannula in subcutaneous tissue. The septum may be configured to be repeatedly pierced by one of the outlet ports in case one infusion set is used per outlet port. For that purpose, the outlet port may comprise a connecting lumen.

As can be seen from FIG. 2 the fluidic paths from the cartridges to the outlet ports are separated. In case the fluidic paths are also separated until the liquid drug enters the patient this may be beneficial in that it is avoided that any undesired liquid drug is administered to the patient because it was remaining in the fluidic path from a previous administering: the drug insulin that may be comprised in the first reservoir 216 lowers the blood glucose level and the drug glucagon that may be comprised in the second reservoir makes the liver releasing glucose into the blood stream to raise the blood glucose level. Thus, the scenario would be avoided in which a patient already has a blood glucose level that is too low in which case the device would inject glucagon, and in which scenario it is thus desired to avoid injecting more insulin by flushing the tubing that goes to the patient.

Preferably depending on the used drugs, in an alternative it may be possible that a single infusion set is used, wherein the two outlet ports 228 and 226 are brought together for being connected to this single infusion set.

The drug delivery device 100 further comprises a sensor or analyzer 220 which is adapted to determine the type of liquid drug retained in any of the first reservoir 216 and the second reservoir 218. One reason may be that two different kinds of drugs may be contained in the reservoir 216 and in the reservoir 218. One type of drug like insulin may lower blood glucose levels, while another type of drug like glucagon may increase blood glucose levels. Since the drug dosing scheme 206 specifies that for example at a certain time either insulin or glucagon has to be administered to the user 90 with a certain dosage, the device have to ensure that an accidental confusion of the two types of drug is avoided.

Figure 4:
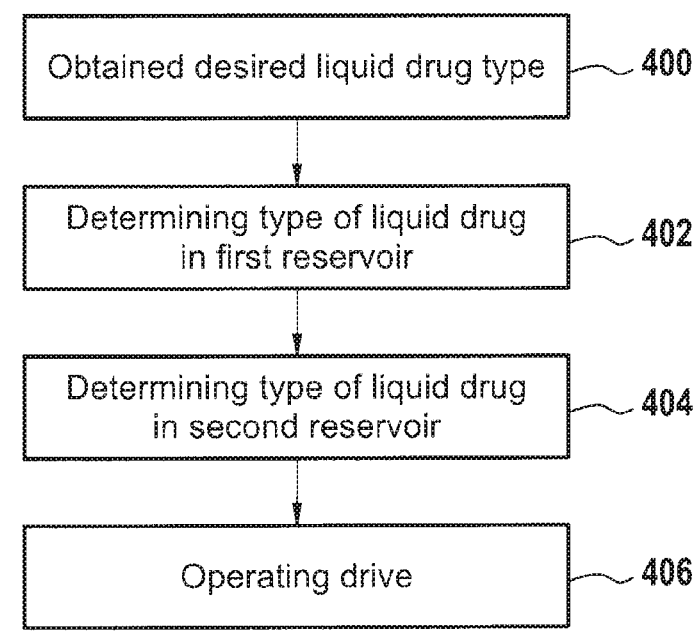
FIG. 4 is a flowchart illustrating the operation of the drug delivery device.

As described with respect to the flowchart in FIG. 4, in step 400 the device 100 may obtain the desired liquid drug type from the memory 204, i.e., the desired drug type 208 is read from the memory 204. Thereupon, in step 402 the type of liquid drug that is currently retained in the first reservoir 216 is determined using the sensor 220. Similarly, in step 404 the type of liquid drug that is currently retained in the second reservoir is determined using the sensor 220.

For example, in case the drug dosing scheme 206 specifies that the desired drug 208 is insulin and further in case step 402 resulted in the outcome that the first reservoir 216 comprises insulin, step 406 is an operation of the drive 224 in such a manner that the insulin contained in the reservoir 216 is provided to the first outlet port 226, while the drug contained in the second reservoir is not used at that moment.

In the most general manner, the user of the drug delivery device 100 is completely free of which type of drug is contained in which reservoir and in which order the reservoirs are inserted into the sockets 215 and 217, respectively. There are various possibilities how the sensor or analyzer 220 can determine the type of drugs contained in the reservoirs. In one example, each reservoir carries a respective tag that is readable by the sensor 220. For example, the tag may be optically readable and may indicate in alphanumeric letters the type of liquid drug that is contained in the reservoir. In this example, the sensor 220 may be a camera. In another example, the tag may be readable using radio communication, wherein the tag is for example an RFID tag. In a further example, the sensor 220 may be adapted to directly determine the physical or chemical properties of the liquid drug contained in the reservoirs by performing a respective measurement. As can be readily appreciated by those of skill in the art, the term "sensor" as used herein is to be construed broadly, covering readers such as optical readers that can read information such as identification tags printed or otherwise present on the reservoirs and also covers any of a wide variety of sensing or analysis devices that can detect or analyze physical and chemical properties of the liquids within the reservoirs.

Even though the example of FIG. 2 depicts the connection of the sensor 220 with the reservoirs 216 and 218, respectively, it will be understood that the sensor 220 may also perform said measurements when being connected to any part of the fluid paths between the respective reservoir's and the drug outlet ports 226 and 228, respectively.

The flowchart that was discussed with respect to FIG. 4 assumed that one of the first and second reservoirs contains the desired liquid drug type. In contrast thereto, the flowchart in FIG. 5 also considers the possibility that none of the first and second reservoirs contains the desired liquid drug type. In FIG. 5, the method starts again with step 500 and obtaining the desired liquid drug type from the memory 204. Thereupon, in steps 502 and 504, respectively, the types of liquid drugs contained in the first and second reservoir are determined. Thus, steps 502-504 are the same as the steps 400-404.

In addition, in step 506 it is determined if any of the determined drug types correspond to the desired liquid drug types. In case the desired liquid drug type and the determined liquid drug types do not match, the device 100 provides the warning signal in step 512 to the user via the user interface 214. Additionally, the device is operated in such a manner that none of the drugs contained in the reservoirs is accidently administered to the user 90.

However, in case in step 506 it is determined that at least one of the determined liquid drug types matches the desired liquid drug type, the method continues with steps 508 and 510 of operating the drive. Step 508 corresponds to the step 406 which was discussed with respect to FIG. 4.

Figure 6:
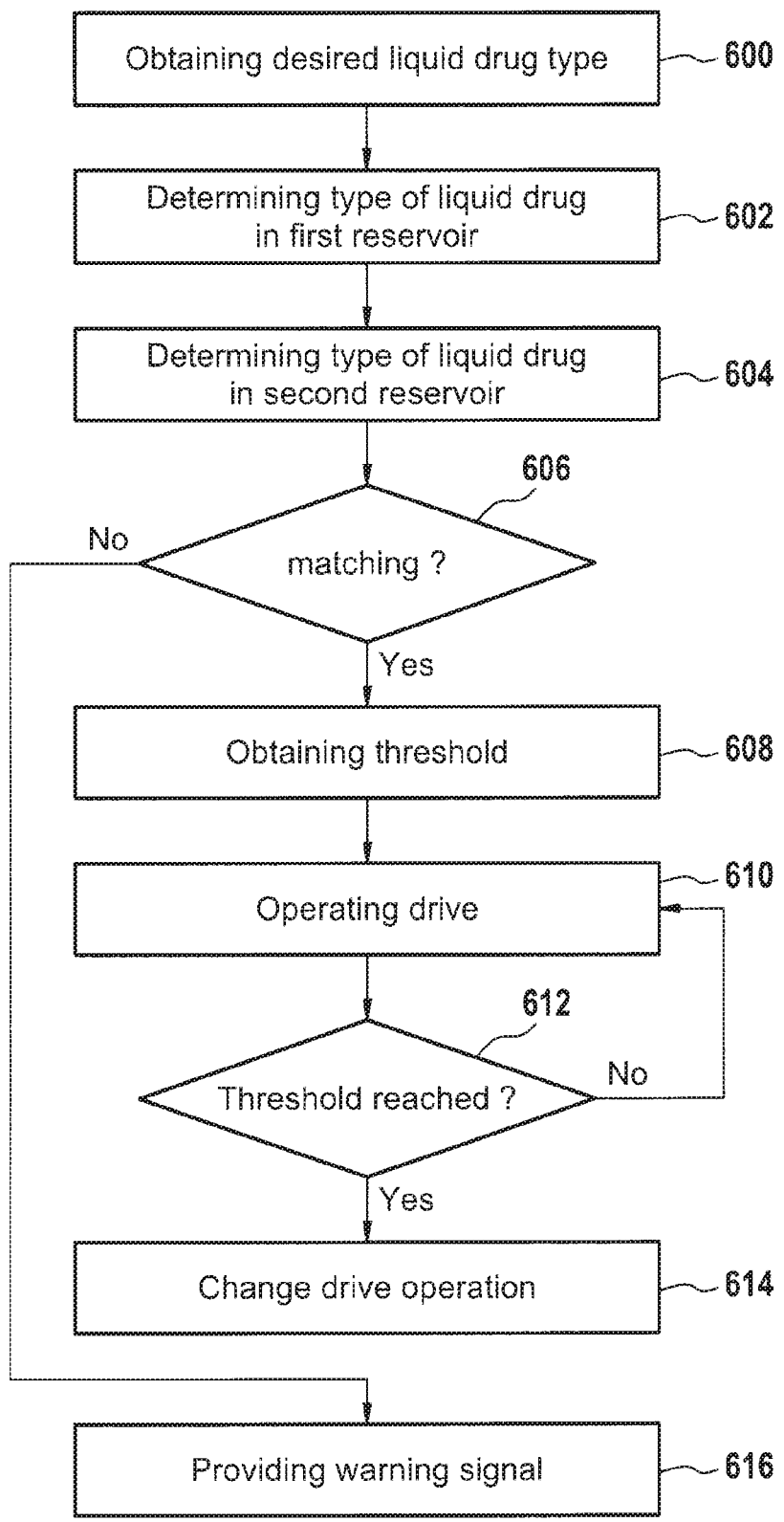
FIG. 6 is a flowchart illustrating another operation of the drug delivery device.

In the flowchart depicted in FIG. 6 a further scenario of usage of the drug delivery device 100 is discussed, wherein it is assumed that the two reservoirs 216 and 218 may retain the same type of liquid drug. Again, the method starts with steps 600, 602 and 604, in which the desired liquid drug type is obtained from the memory 204, the type of liquid drug contained in the first reservoir and the type of liquid drug contained in the second reservoir are determined. Again, these steps correspond to steps 400 to 404 of FIG. 4.

Figure 5:
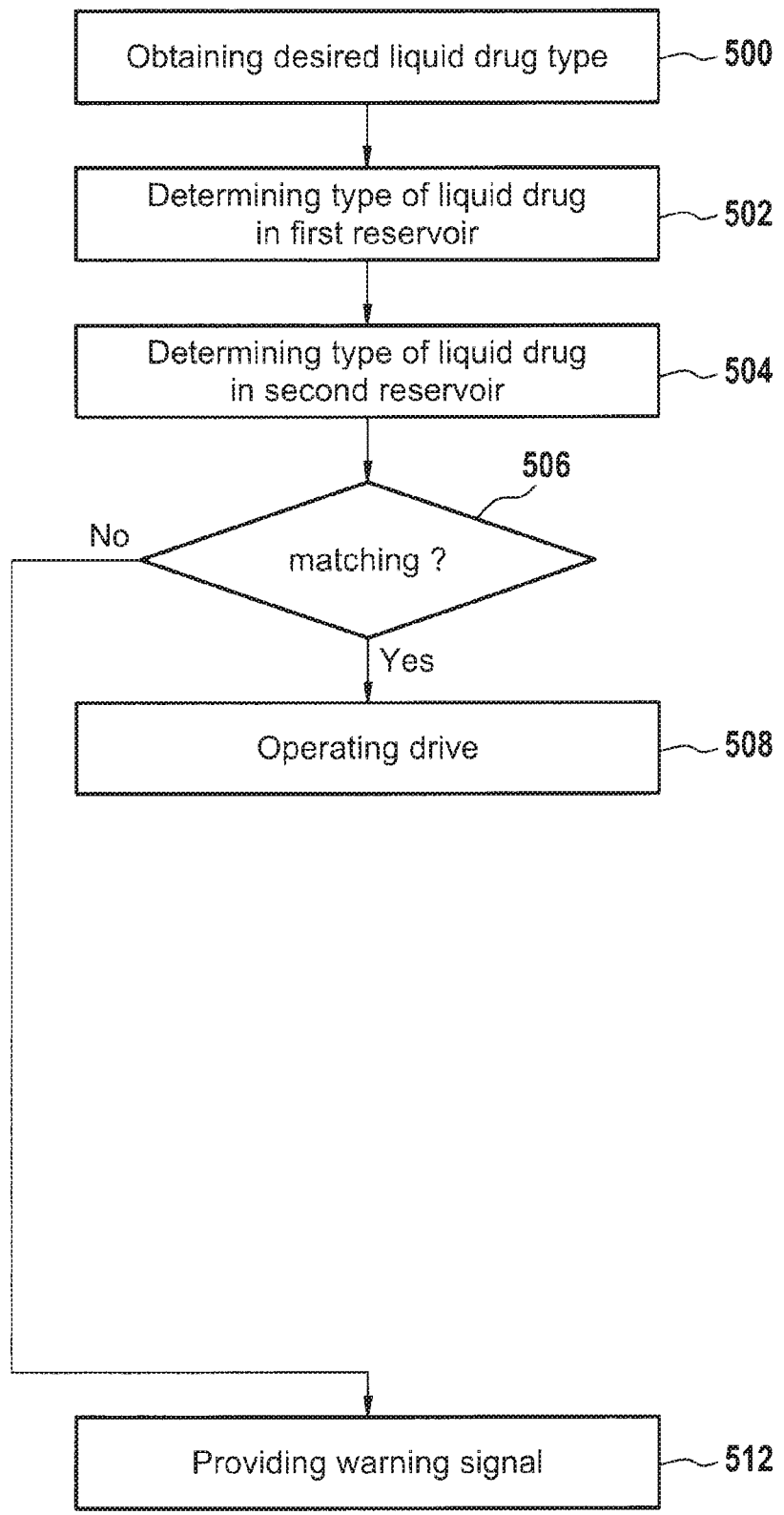
FIG. 5 is a flowchart illustrating the further operation of the drug delivery device.

Step 606 corresponds to step 506 of FIG. 5 where it is determined again, if any of the liquid drug types contained in the reservoirs is matching the desired liquid drug type. If there is no matching, the method terminates with step 616 and the provision of warning signal via the user interface 214. This corresponds to step 512 of FIG. 5.

However, in case both reservoirs contain the same a liquid drug which type corresponds to the desired liquid drug type, the method continues with step 608 and the obtaining of the threshold from the memory 204. The threshold indicates a criterion upon which the device has to switch from providing the liquid drug from the first reservoir to providing the liquid drug from the second reservoir.

In an example, the drug delivery device 100 knows from the dosage 210 which amount of the liquid drug is to be administered to the user 90 per bolus. The threshold may indicate that in case the amount of drug that is currently remaining in the first reservoir is smaller than said bolus, the device 100 has to operate the drive such that for the next bolus administration the drug is provided from the second reservoir 218.

After having obtained the threshold in step 608, in step 610 the drive is operated as it was discussed before with respect to step 508 or step 406. It has to be noted here that the obtaining of threshold in step 608 may be performed at any time before performing the step 612 in which it is checked if the threshold is reached. In case step 612 results in that the threshold was not yet reached, the operation of the drive with step 610 continues unmodified. However, in case in step 612 it is determined that the threshold is reached, the method continues with step 614 and the changing of the operation of the drive in such a manner that the drive does not expel the liquid drug any more from the first reservoir but does now expel the liquid drug from the second reservoir. Thereupon, the drive is operated in accordance with the dosing scheme 206.

Figure 3:
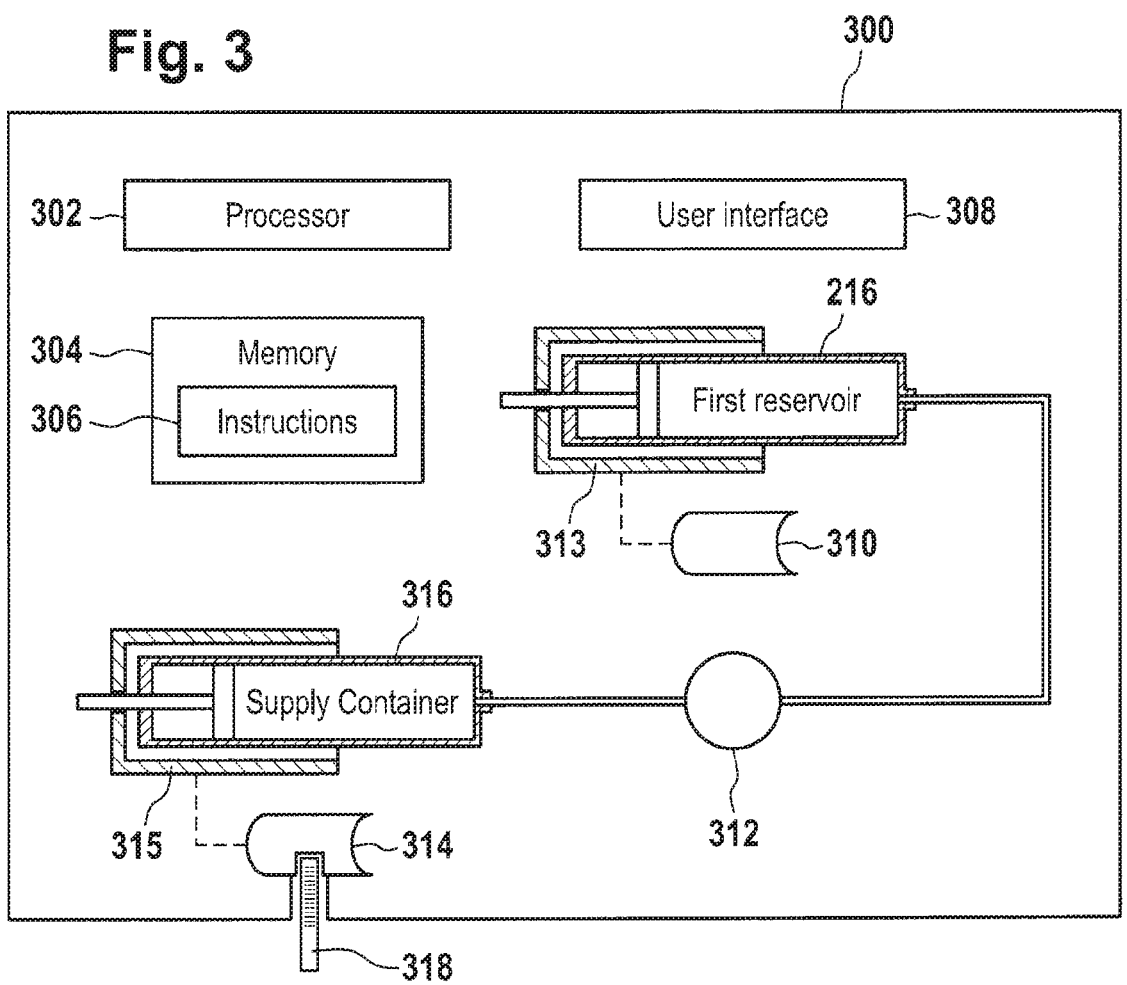
FIG. 3 is the schematic block diagram of a transfer station for transferring a liquid drug between a supply container and a reservoir.

FIG. 3 depicts a block diagram of the transfer station 300 for transferring a liquid drug between the supply container 316 and a reservoir 216, for example the first reservoir 216 that was discussed with respect to FIG. 2. However, the first reservoir is just an example and in a similar manner the second reservoir may be filled using the transfer station 300. The first reservoir 216 and the supply container 316 are received by the transfer station using respective sockets 313 and 315, respectively.

The transfer station 300 comprises the processor 302 and a memory 304 comprising instructions 306 that are executable by the processor 302. Execution of the instructions causes the transfer station 300 to perform the method, as it is for example described in the flowchart of FIG. 7.

Figure 7:
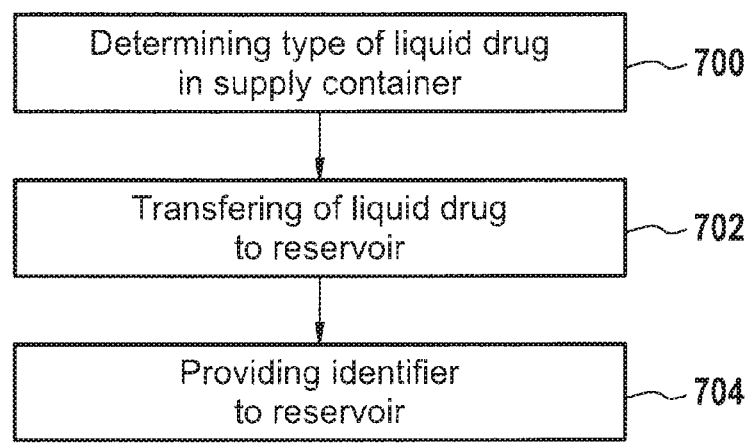
FIG. 7 is the flowchart illustrating an operation of the transfer station.

In step 700 of FIG. 7, the transfer station determines the type of liquid drug that is currently retained in the supply container 316. The determination of the type of liquid drug is performed using a sensor 314, which may be provided, e.g., as an analyzer or measurement cell. Here, the same principles apply in an analogous manner as it was discussed with respect to the drug delivery device 100 and FIG. 2. For example, the supply container 316 may carry a tag which indicates in an optically readable manner the type of drug that is retained by the supply container 316. Alternatively or additionally, the type of drug may be determined by a physical or chemical analysis of the drug either in the fluid path between the supply container and the first reservoir 216 or directly in the supply container 316 or in the measurement cell 314 connected or attached to the supply container 316 or in a measurement cell connected or attached to the reservoir 216.

For example, the measurement cell 314 may be adapted to receive a test strip 318 containing a reagent which is chemically reactive to a certain type of active substance of a drug. While the measurement cell 314 is the fixed part of the transfer station 300, the test strip 318 is a disposable part such that one test strip can be used for each process of transfer of liquid drug from the supply container 316 to the reservoir 216. The reagent of the test strip will react with the drug in a manner, which is detectable by a sensor of the transfer station 300. For example, the transfer station 300 may comprise an optical sensor which determines the resulting coloring of the test strip 318 as a result of the chemical reaction of the drug with the reagent.

After having determined the type of liquid drug that is contained in the supply container in step 700, the method continues with step 702 in which the liquid drug is transferred from the supply container 316 to the first reservoir 216. The transfer of the liquid drug can either be performed in an automated manner using a pump 312 in the fluid path between the supply container and the first reservoir. Alternatively it is possible, that the user manually pushes or pulls the drug from the supply container to the first reservoir using a respective piston of the reservoir or the supply container.

It has to be understood that the presence of the pump also encompasses the possibility that the first reservoir may comprise a piston, as described in FIG. 2. By automatic or manual pulling of the piston, the volume for receiving the drug is increased such that the drug is sucked inside the first reservoir 216. This respective piston of the reservoir may be the same piston, which is used in the drug delivery device 100 to push the liquid towards the outlet port 226 or 228, respectively.

At any time after step 700 and the determination of the type of liquid drug that is or was contained in the supply container, an identifier is provided to the first reservoir 216, the identifier specifying the determined type of liquid drug. For example, the identifier may be printed onto the reservoir using a respective printer 310. In case the identifier is provided to the reservoir using a near field communication tag assigned to the reservoir, the storing of the identifier in the near field communication tag is performed using a respective sender module. In this case, reference numeral 310 would indicate this sender module. Other types of providing the identifier like magnetic storage, electronic storage or mechanical modification of a predefined area of the reservoir are also possible.

As will be appreciated by one skilled in the art, aspects of this disclosure may be embodied as an apparatus, method or computer program product. Accordingly, aspects of this disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of this disclosure may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of this disclosure. Computer executable code for carrying out operations for aspects of this disclosure may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure are described with reference to flowchart illustrations and/or block diagrams of methods, apparatus (systems) and computer program products according to embodiments of this disclosure. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

| REFERENCE NUMERALS | |
| --- | --- |
| 90 | user |
| 100 | drug delivery device |
| 102 | skin |
| 202 | processor |
| 204 | memory |
| 206 | dosing scheme |
| 208 | desired drug |
| 210 | dosage |
| 212 | instructions |
| 214 | user interface |
| 215 | sockets |
| 216 | first reservoir |
| 217 | socket |
| 218 | second reservoir |
| 220 | sensor or measurement cell |
| 223 | plunger |
| 224 | drive |
| 225 | piston |
| 226 | outlet port |
| 228 | piston |
| 300 | transfer station |
| 302 | processor |
| 304 | memory |
| 306 | instructions |
| 308 | user interface |
| 310 | printer |

| REFERENCE NUMERALS | |
| --- | --- |
| 312 | pump |
| 313 | socket |
| 314 | measurement cell |
| 315 | socket |
| 316 | supply container |
| 318 | strip |

What is claimed is:

1. A method for operating a drug delivery device having first and second liquid drug reservoirs, first and second outlet ports, and a drive configured for expelling liquid drug from the first and second reservoirs to first and second outlet ports, respectively, the method comprising:
   storing in a memory a drug dosing scheme specifying a desired liquid drug type;
   using a sensor to analyze at least one of a physical or chemical property of the first and/or second liquid drug to thereby detect information concerning the type of liquid drug contained in the first and/or second reservoir; and
   using a processor to:
   (i) receive the information from the sensor and thereby determine the type of liquid drug retained in the first reservoir and/or the second reservoir, and
   (ii) use the drug dosing scheme and the determined type of liquid drug to operate the drive,
   wherein the method further comprises using the processor to:
   operate the drive to deliver the liquid drug from the first reservoir to the first outlet port;
   determine the amount of the drug in the first reservoir currently available to the user;
   compare the determined amount with the threshold criterion; and
   in response to the comparison, when the determined amount is lower than or equal to the threshold criterion, operate the drive to deliver the liquid drug from the second reservoir to the second outlet port, the threshold criterion specifying a residual availability of the drug provided in the first reservoir.

2. The method of claim 1, further comprising using the processor to operate the drive to deliver the desired liquid drug from the first reservoir or second reservoir to the respective first or second outlet port.

3. The method of claim 1, wherein the stored drug dosing scheme specifies that the first reservoir must contain the desired liquid drug type, the method further comprising:
   when the first liquid drug determined to be in the first reservoir does not correspond to the desired liquid drug type, the processor provides a warning signal via a user interface; and
   the processor prevents delivery from the first reservoir to the first outlet port.

4. The method of claim 1, wherein the stored drug dosing scheme specifies that the first reservoir or the second reservoir must contain the desired liquid drug type, the method further comprising:
   when neither the first liquid drug nor the second liquid determined to be in the first and second reservoirs, respectively, corresponds to the desired liquid drug, the processor provides a warning signal via a user interface; and
   the processor prevents delivery from the first and second reservoirs.

5. The method of claim 1, further comprising delivering the same liquid drug from the first and second reservoirs.

6. The method of claim 1, further comprising:
assigning identifiers to the first reservoir and the second reservoir specifying the type of liquid drug retained therein; and
determining the type of the liquid drug retained in the first reservoir and the second reservoir by using the sensor to read the identifiers.

7. The method of claim 1, wherein the step of using the sensor comprises analyzing a physical property of the first and/or second liquid drug.

8. The method of claim 1, wherein the first and second liquid drugs are different, the method further comprising maintaining separate (i) a first fluid pathway from the first reservoir to the first outlet to a user from (ii) a second fluid pathway from the second reservoir to the second outlet to the user.

9. A drug delivery device, comprising:
first and second liquid drug reservoirs;
first and second outlet ports;
a drive configured for expelling a first liquid drug from the first reservoir to the first outlet port and for expelling a second liquid drug from the second reservoir to the second outlet port;
a memory having a drug dosing scheme specifying a desired liquid drug type;
a sensor configured to analyze at least one of a physical or chemical property of the first and/or second liquid drug to thereby obtain information concerning the type of liquid drug contained in the first and/or second reservoir; and
a processor configured to:
(i) receive the information from the sensor and thereby determine the type of liquid drug retained in the first reservoir and/or the second reservoir, and
(ii) use the drug dosing scheme and the determined type of liquid drug to operate the drive,
wherein the first and second reservoirs are configured to deliver the same liquid drug and wherein the processor is further configured to:
operate the drive to deliver the liquid drug from the first reservoir to the first outlet port;
determine the amount of the drug in the first reservoir currently available to the user;
compare the determined amount with the threshold criterion; and
in response to the comparison, when the determined amount is lower than or equal to the threshold criterion, operate the drive to deliver the liquid drug from the second reservoir to the second outlet port, the threshold criterion specifying a residual availability of the drug provided in the first reservoir.

10. The drug delivery device of claim 9, wherein the processor is configured to operate the drive to deliver the desired liquid drug from the first reservoir or second reservoir to the respective first or second outlet port.

11. The drug delivery device of claim 9, wherein the drug dosing scheme specifies that the first reservoir must contain the desired liquid drug type, wherein when the first liquid drug determined to be in the first reservoir does not correspond to the desired liquid drug type, the processor is configured to provide a warning signal via a user interface, wherein the processor is further configured to prevent delivery from the first reservoir to the first outlet port.

12. The drug delivery device of claim 9, wherein the drug dosing scheme specifies that the first reservoir or the second reservoir must contain the desired liquid drug type, wherein when neither the first liquid drug nor the second liquid drug determined to be in the first and second reservoirs, respectively, corresponds to the desired liquid drug, the processor is configured to provide a warning signal via a user interface, wherein the processor is further configured to prevent delivery from the first and second reservoirs.

13. The drug delivery device of claim 9, wherein the first reservoir and the second reservoir have assigned identifiers specifying the type of liquid drug retained therein, the determination of the type of the liquid drug retained in the first reservoir and the second reservoir comprising the sensor reading the identifiers.

14. The drug delivery device of claim 9, wherein the sensor is configured to analyze at least one chemical property of the first and/or second liquid drug.

15. The drug delivery device of claim 9, comprising (i) a first fluid pathway from the first reservoir to the first outlet to a user and (ii) a second fluid pathway from the second reservoir to the second outlet to the user, wherein the first and second fluid pathways are maintained separate.

16. A method of operating a system having a transfer station and a drug delivery device, the method comprising:
analyzing by the transfer station a liquid drug contained in a supply container to analyze at least one of a physical or chemical property of the liquid drug to thereby determine the type of liquid drug retained in the supply container;
transferring the liquid drug from the supply container to a first reservoir of the drug delivery device;
providing an identifier for the first reservoir, the identifier specifying the type of liquid drug retained in the supply container;
using the drug delivery device to determine the type of liquid drug retained in the first reservoir; and
in accordance with a drug dosing scheme, using a processor of the drug delivery device to:
(i) receive the information from the sensor and thereby determine the type of liquid drug retained in the first reservoir and/or a second reservoir, and
(ii) use the drug dosing scheme and the determined type of liquid drug to operate the drive.

17. The method of claim 16, wherein the step of analyzing the liquid drug comprises analyzing a physical property of the liquid drug.

18. The method of claim 16, wherein the step of providing the identifier comprises one or more of:
printing the identifier onto the reservoir;
storing the identifier in a near field communication tag assigned to the reservoir;
storing the identifier in a magnetic tag assigned to the reservoir;
electronic storing of the identifier in a chip assigned to the reservoir;
mechanical modification of a predefined area of the reservoir.

19. The method of claim 18, further comprising transferring the liquid drug from the supply container to the reservoir.

* * * * *